US00PP34305P3

(12) United States Plant Patent
Shipley

(10) Patent No.: US PP34,305 P3
(45) Date of Patent: Jun. 7, 2022

(54) ***ASCLEPIAS SUBULATA* PLANT NAMED 'BUTTERFLY MAGIC'**

(50) Latin Name: *Asclepias subulata*
Varietal Denomination: Butterfly Magic

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 16/974,130

(22) Filed: Oct. 14, 2020

(65) Prior Publication Data

US 2022/0117128 P1 Apr. 14, 2022

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
See application file for complete search history.

*Primary Examiner* — Susan McCormick Ewoldt

(57) ABSTRACT

A new and distinct *Asclepias* subulata named 'Butterfly Magic' is characterized by uniform growth habit and plant form, Slightly thicker stems than typical for the species, improved growth and survival in cultivation, greater stem numerical density, faster growth with ultimately increased plant size and improved cold hardiness and survivability.

5 Drawing Sheets

Latin name: *Asclepias subulata.*
Varietal Denomination: 'Butterfly Magic'.

BACKGROUND OF THE INVENTION

*Asclepias subulata*, also known as desert milkweed, rush milkweed, ajamete, or skeleton milkweed is a semi-woody, succulent perennial plant native to southern Arizona, southeast California, southern Nevada, northwest Sonora, and Baja California Norte. Plants generally occur growing along dry washes and declivities within the Sonoran and Mohave Deserts at elevations below about 3000 feet elevation. Desert milkweed is a mostly upright, many stemmed plant growing from about 2-4 feet wide and tall, depending upon growing conditions.

The plants have long been used in traditional medicine by indigenous peoples as an anti-inflammatory and anti-cancer treatment. Recent research has confirmed anti-cancer activity of several compounds found in the extract from this plant. The plants produce latex and were evaluated for rubber production in the early 20$^{th}$ century.

*Asclepias subulata* is an important larval plant food for queen and monarch butterflies wherever it grows. Flowers of desert milkweed produce abundant nectar and are an important nectar food plant especially for butterflies and the tarantula hawk wasp.

Desert milkweed has become a fairly commonly planted landscape plant in the southwestern United States for at least 30 years. The plants are used as drought tolerant accents which attract butterflies and other pollinators. Desert milkweed is also a useful plant for revegetation projects since it can survive with little supplemental water once established throughout climates similar to those encountered in its natural range. *Asclepias subulata* used for landscaping and revegetation projects is generally propagated by seed and has not been previously intentionally selected for superior cultivars.

The present invention relates to a new and distinct cultivar of *Asclepias subulata*. The cultivar originated from a mixed seed collection of *Asclepias albicans* and *Asclepias subulata* found in wild populations growing in the Transverse Ranges of southern California and purchased from a commercial seed source and received as *Asclepias albicans*. The seed growout clearly indicated the mixed nature of the seeds, as *Asclepias albicans* has stems many times the diameter of those of *Asclepias subulata*. Also, the seedlings of each species showed wide variation in growth form, vigor and general adaptability to cultivation. The seedling plants were grown outdoors near Sahuarita, Ariz. From these seedling plants several selections of both species present in the original seed lot were made based upon characters including improved growth, adaptability to cultivation and growth form compared the general run of several hundred seedlings. Seeds were collected from these selected plants and were used to create a second growout generation. A great freeze (10° F.) occurred the night of Feb. 15, 2012, which killed all the *Asclepias albicans* plants and all but one of the *Asclepias subulata* plants in the generation 2 growout. The surviving plant was taken note of and moved into a heated greenhouse in order to recover. This single plant subsequently recovered from the freeze injury resulting from that night and is the object of this application.

SUMMARY OF THE INVENTION

Among the features that distinguish the new *Asclepias* cultivar from all other available and commercial varieties of desert milkweed known to the inventor are the following combination of characteristics: Uniform growth habit and plant form, somewhat thicker stems, greater stem numerical density, faster growth, somewhat greater plant size and improved cold hardiness and survivability when compared to seed grown individuals commonly seen in the nursery trade.

The propagation procedure is as follows:

Semi-hardwood cuttings about 4" long containing 2 or more nodes are placed into a 1:10 solution of DIP'N GRO™ for 5 seconds, then planted in grow trays filled with peat media. The trays are placed on bottom heat in a fog house maintained at between 75-85° F. and 92-95% relative humidity with mist about every 30 minutes. The cuttings are fully rooted within around 4 weeks. The foregoing characteristics and distinctions come true to form and are established and transmitted through succeeding propagations at a commercial nursery near Sahuarita, Ariz. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Asclepias subulata* 'Butterfly Magic' growing near Sahuarita, Ariz., depicted in color as nearly correct as it is possible to make in a color illustration of the character.

DETAILED PLANT DESRIPTION

Figure 1:
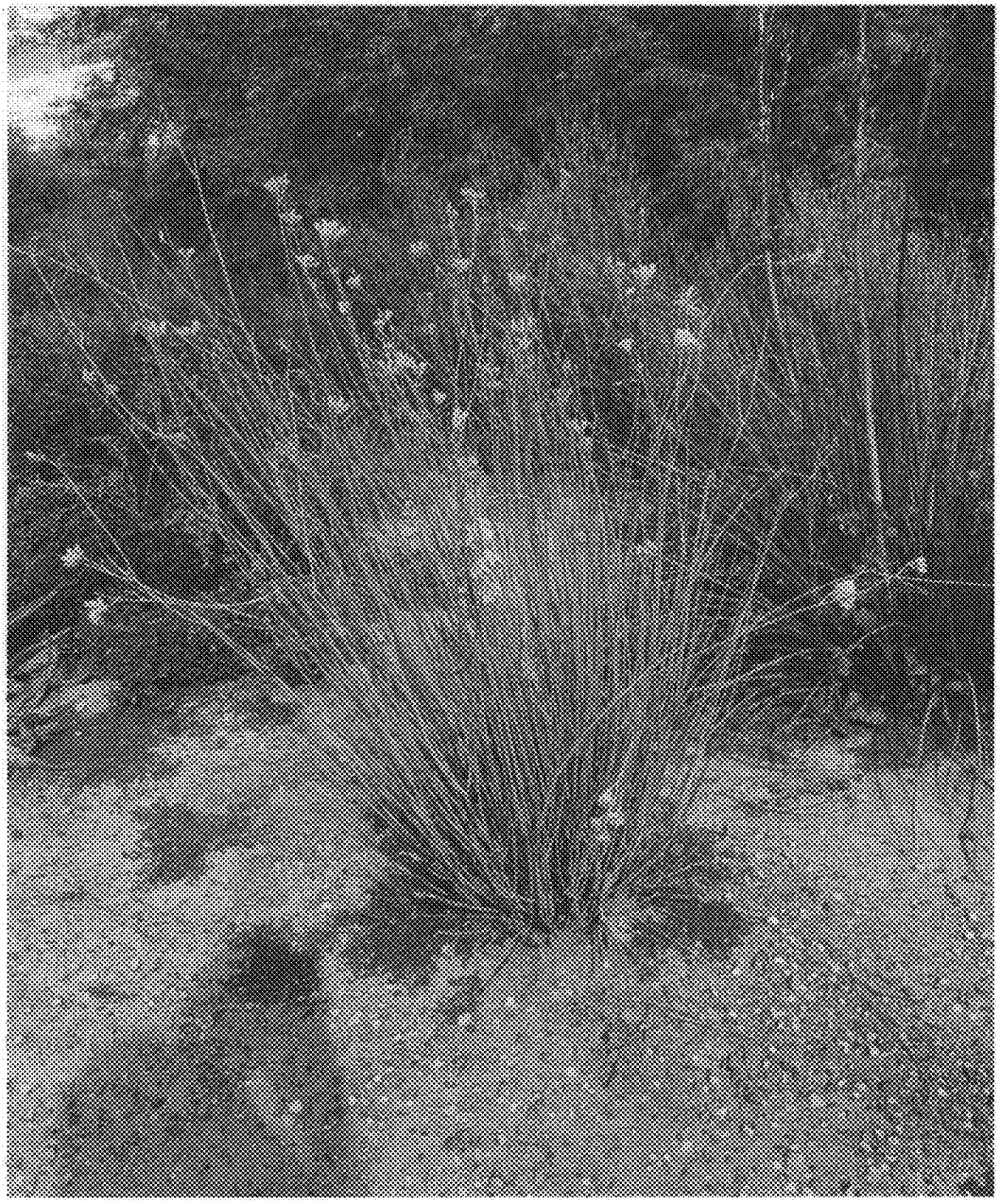
FIG. 1 shows *Asclepias subulata* 'Butterfly Magic' at age 3 years growing at a commercial nursery near Sahuarita, Ariz.
Figure 2:
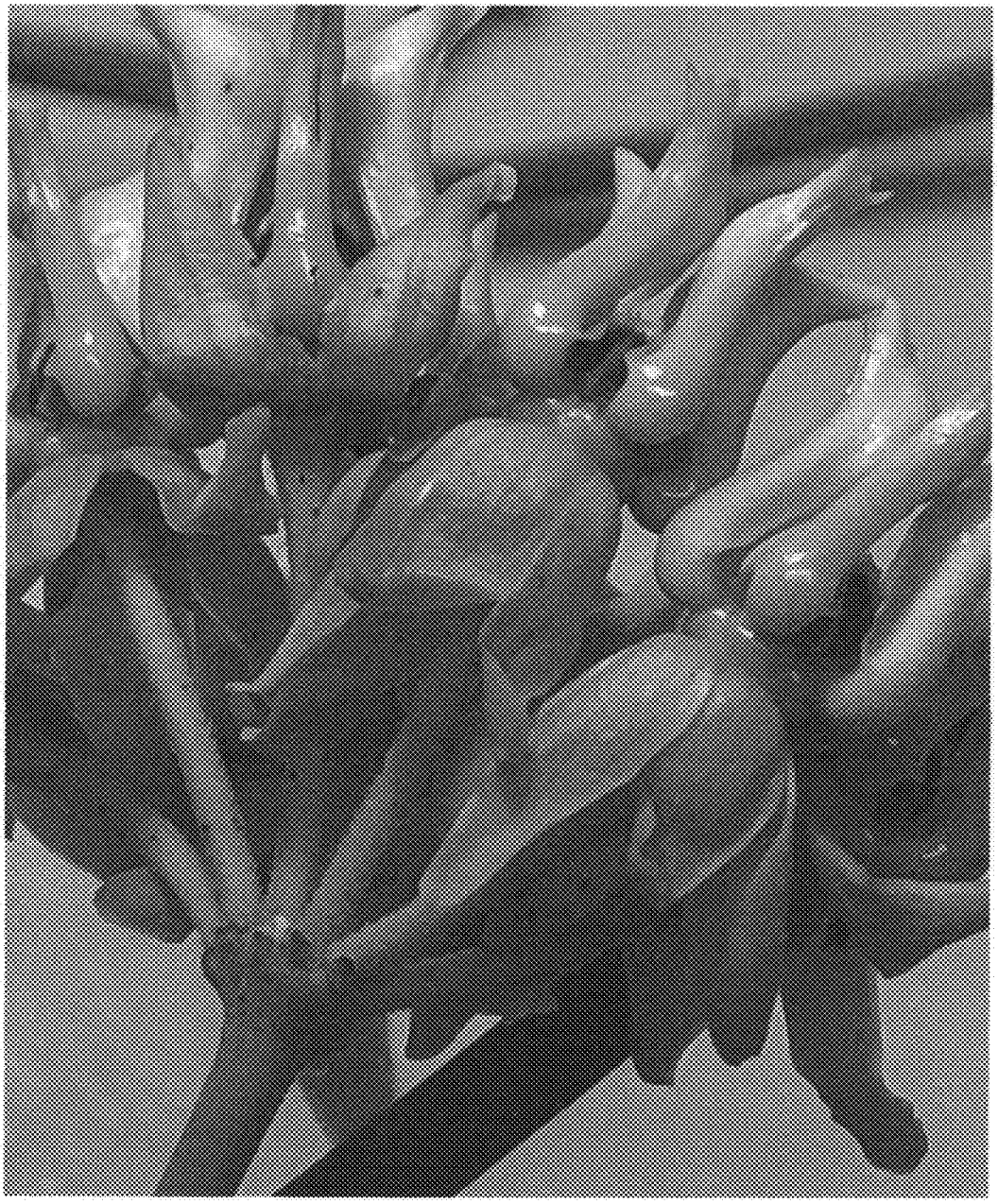
FIG. 2 is a closeup of the inflorescence of *Asclepias subulata* 'Butterfly Magic'.
Figure 3:
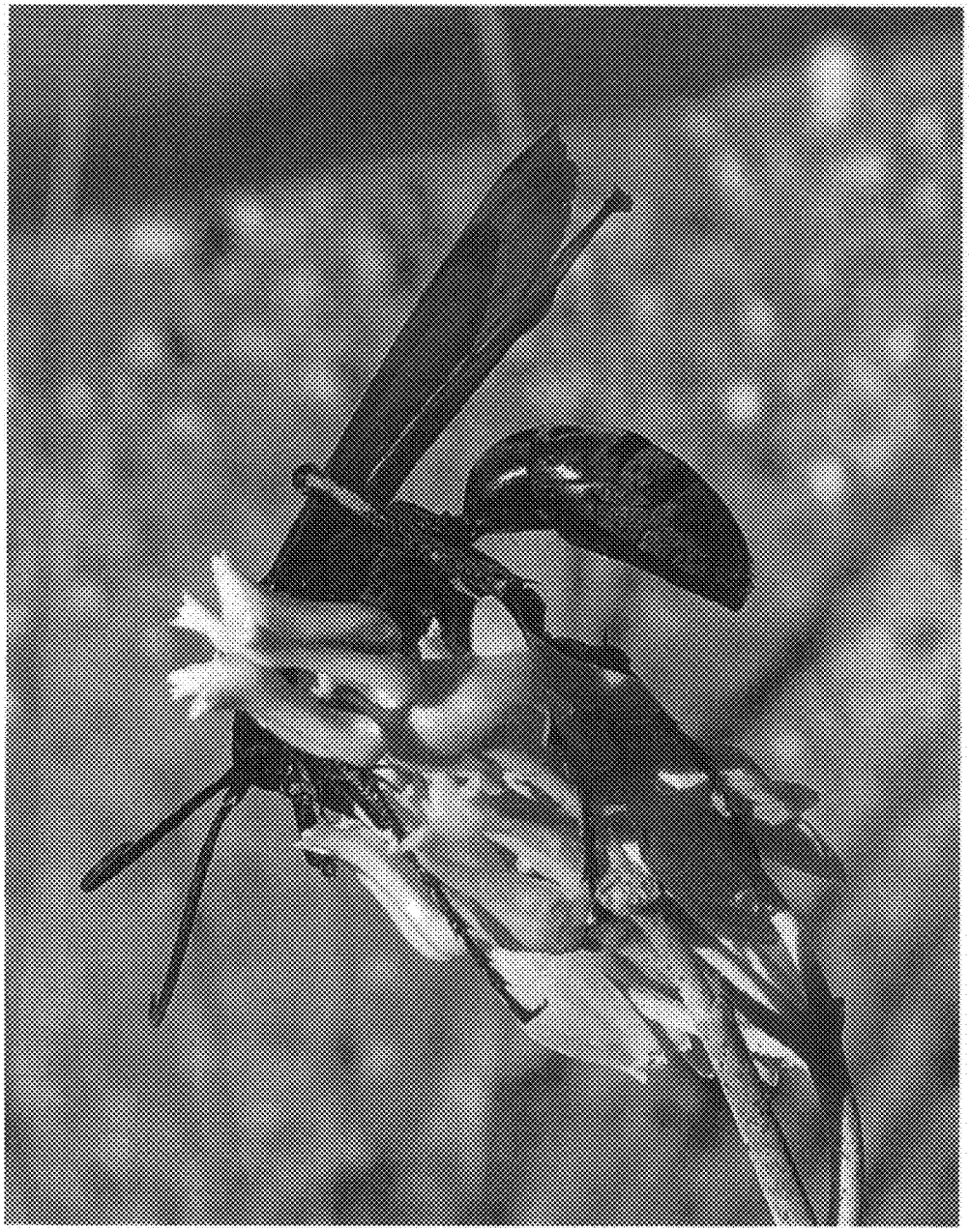
FIG. 3 shows a tarantula hawk wasp pollinating *Asclepias subulata* 'Butterfly Magic'.
Figure 4:
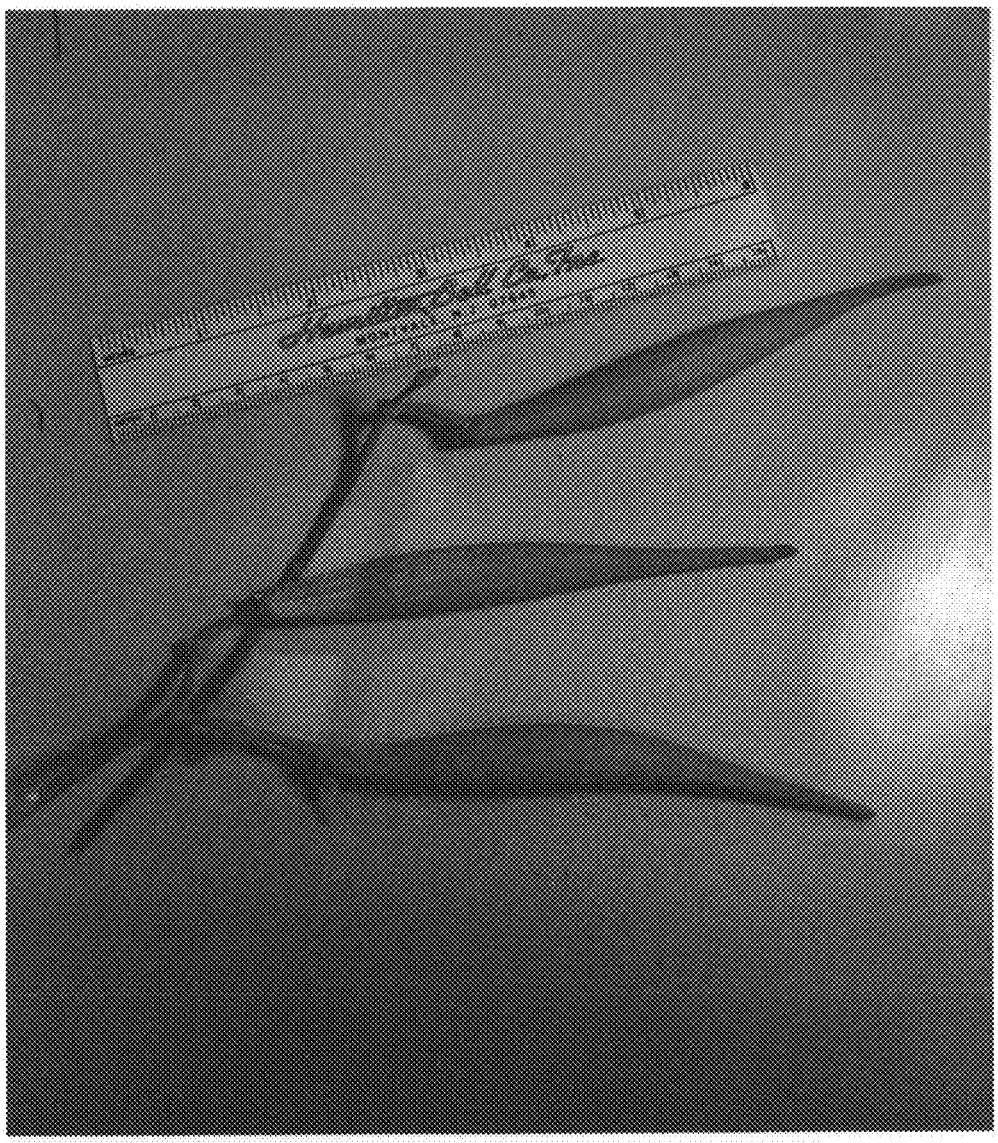
FIG. 4 illustrates the mature fruits of *Asclepias subulata* 'Butterfly Magic'.
Figure 5:
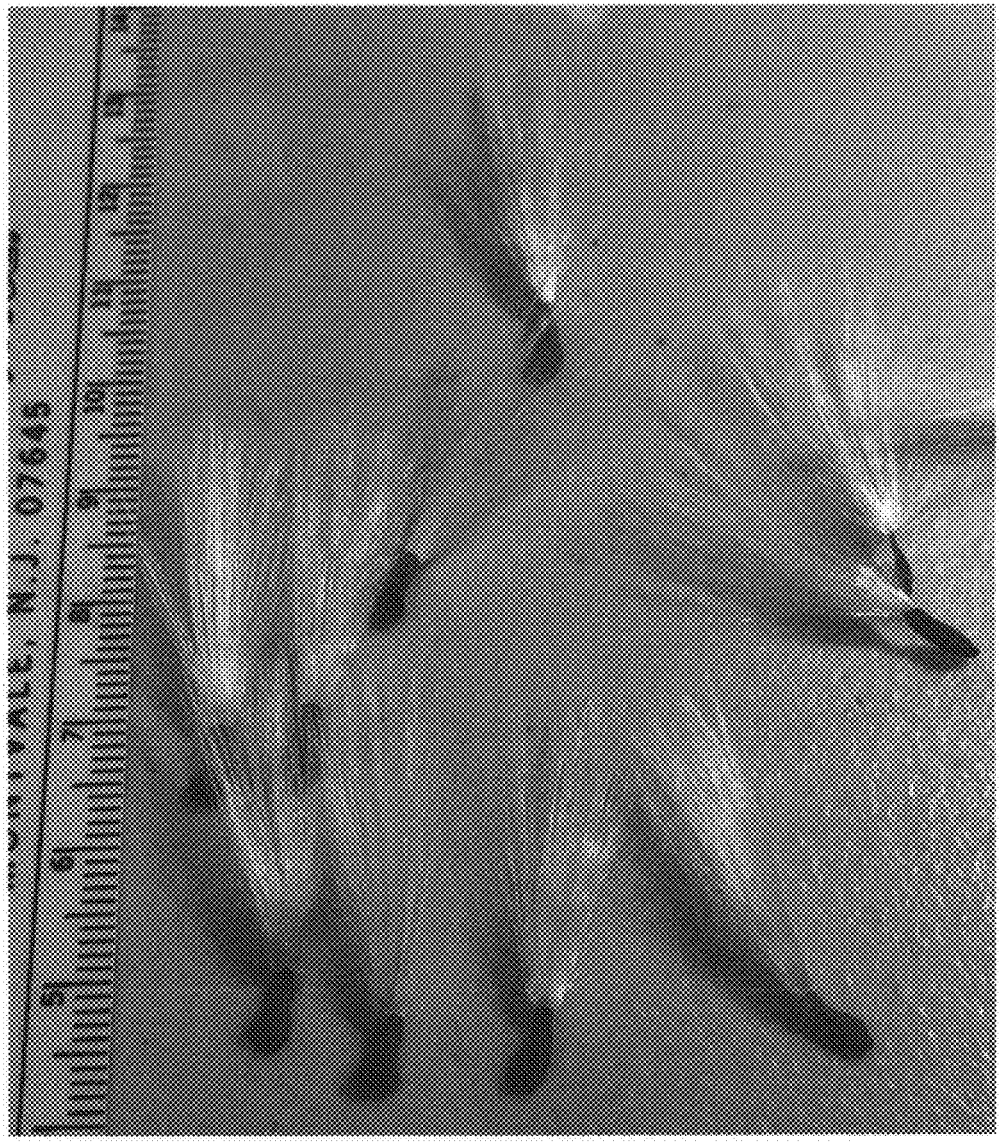
FIG. 5 shows the seeds of *Asclepias subulata* 'Butterfly Magic'.

The following is a detailed description of the new *Asclepias subulata* plant based upon 1-3 year old plants growing in the ground at a commercial nursery near Sahuarita, Ariz.

The color descriptions are based upon the 5$^{th}$ edition RHS Colour Chart, 2007. Color names other than common usage are as listed in *COLOR Universal Language and Dictionary of Names*, by Kenneth L. Kelly and Deane B. Judd; National Bureau of Standards special publication 440. Washington, D.C.; U.S. Department of Commerce, National Bureau of Standards, December 1976.

The plant is a mostly basally, highly branched, woody succulent growing to reach 4 feet tall×5 feet wide at maturity. Some secondary branches do form along the stems with a branch angle of 45-60°. Branches grow mostly close to vertical, but often become arching from their own weight as they lengthen. Mature plants are more or less vase shaped. Above ground plant parts all exude white latex when cut or injured. *Asclepias subulata* 'Butterfly Magic' has slightly thicker stems and a larger, denser and faster growing habit than is typical of the species. Plants grow better both in nursery conditions and in the ground than is typical for the species. The plants are hardy to at least the upper teens °F. and established plants have demonstrated survivability to at least 10° F.

Stems are terete, glabrous, with a base color of 189A. At age 3 years growing in the ground the number of stems exceeds 100. The stems are densely covered with round spots about 30μ in diameter. Spots are colored varying from 189C-189D. The stems have a slightly indented ring encircling the stern at each node, giving an appearance somewhat similar to *Equisetum*.

Internodes vary in length from 13 mm to 75 mm. Young mature branches measure 2-3 mm in diameter eventually thickening to 8 mm in diameter before bark starts to appear. The largest stems at the base of the plant reach a maximum diameter of about 1 cm. At that age and size, the surface is uniformly colored close to 197D, with a somewhat warty surface. Axillary buds are not visible.

Young, growing leaves and stems are colored varying from 152A to 199C. All young growing parts including the stems, leaves, peduncles, pedicels and calyces are covered with soft hairs whiter than 157D which become mostly to completely caducous with maturity.

Mature leaves are opposite, sessile, narrowly linear and measure from 40-60 mm long×0.5-0.75 mm thick and wide. The leaf apex varies from acute to rounded. The leaf margins are entire. The leaf base is slightly clasping at the stem attachment. Leaves are strongly cupped adaxially in cross section. Leaves are glabrous at this stage of growth and are colored uniformly 189A. Leaves are relatively short lived, and often only present under favorable moisture conditions and during growth spurts.

Inflorescence is a 5-12 flowered umbel, alternating from each node down the branches near the terminal portions.

Peduncles at the time of blooming are terete and diverge at about a 45° angle from the branch axis. These measure from 11-14 mm long×1.5-2 mm thick at that time. Peduncles vary in color from138B to 138C and are covered with scattered caducous hairs whiter than 157D. By the time of green fruit maturity, the peduncles have variously curved downward from the weight of the fruits, often curving from 45° from the stem axis to nearly perpendicular to it. At this time the peduncles typically measure about 10 mm long×2 mm thick. Peduncle is colored 194D at fruit green maturity and still has some scattered, fine, mostly straight, ascending hairs. By the stage of full dry maturity, the hairs are gone.

Pedicels at bloom time are terete, covered with more or less appressed, ascending hairs colored whiter than 157D. Pedicels are colored 138D at anthesis. Pedicels measure from 8-11 mm long×1 mm thick at anthesis.

Mature, unopened buds are rounded, 5 angled, and more or less ovoid in shape. The bud appears to be variable in color with growth conditions, although within a given umbel or bud the color seems relatively uniform. Color ranges from 144D to 154D and is sometimes tinged with 63C near the sunward apex. Buds measure 9-11 mm long×7 mm in diameter.

The calyx is visible at the lower portion covering the base of the bud. The calyx is comprised of 5 broadly acute triangular sepals that are free to the receptacle, margins entire, colored 138D. The adaxial surface is glabrous while the abaxial surface is moderately sericeous, hairs whiter than 157D. Sepals measure 3 mm long×1.5 mm wide.

The corolla is variable in color depending upon growth conditions, but petals vary between the colors of 144D to 154D. Petals are broadly lanceolate, entire, glabrous and sometimes have a slight indentation at the apex. Petal margins are entire and somewhat scarious. A vaguely defined but raised central nerve is visible on the abaxial side of the petal. Petals are very strongly reflexed at anthesis.

The gynostegium is more or less vase shaped measuring 10 mm long×7 mm wide including the hoods. Hoods are sigmoid and axially enrolled with 3 acute teeth at the apex.

The 5 glabrous and somewhat shiny hoods are colored uniformly 157B except near the base where the color transitions to 65D. Hoods measure 9-10 mm long and about 2.5 mm wide at the base. The outer 2 teeth are 0.8 mm long, while the center tooth is 0.5 mm long. Beaks (horns) are hooked axially and measure 0.9 mm long×0.4 mm wide, acutely tapering to the tip, color 157B.

Gynostegium with hoods removed is 5 angled, measuring 3 mm long×3 mm wide, the apex colored 157B. Ribs alternate with the hood attachments, and are raised, especially toward the base, glabrous, fairly lustrous, entire, each rib split lengthwise from the base at least ⅓ of the length. Ribs are colored 152C. Two veils alternate with each rib, colored N187C.

Pollinia are paired, each measuring 1 mm long×0.5 mm wide×0.1 mm thick, reniform, color closest to 165A.

The ovary contains two ovules, each capable of producing a many seeded follicle, although more commonly only one of the two reaches maturity. Generally, only one or two fruits will set on each inflorescence. Young, developing fruits are colored 152A and the surfaces are sericeous.

The following fruit description is based upon at fruits at green physiological maturity, as the fruits had not yet dried sufficiently to turn to its ultimate color at dehiscence. Color of the dry ripe fruit derived from a dehisced follicle is listed at the end. Fruit a terete lanceoloid follicle measuring from 74-109 mm long×9-13 mm in diameter, color closest to 193A. Surface subtly 16-18 grooved, the lines running the length of the fruit, the surface sparsely puberulent, the hairs mostly erratic. The fruit also has scattered rounded glands that are slightly raised and measure 0.25-0.5 mm in diameter. The glands are colored 71A. Fruit is bluntly acute at the base and has a long tapering apex. The calyx remains attached at fruit maturity, 5 lobed, the lobes acute, more or less triangular, with a raised central nerve. The lower abaxial half is covered with forward appressed hairs, while the upper half is glabrous. Abaxial sepal color is 199D. Sepal adaxial surface is glabrous, color 199D. Sepals measure 3-3.5 mm long×2-3 mm wide.

The fruit dehisces along one suture at dry maturity to release wind borne seeds. The fruit exterior when dry is colored 163D, while the smooth interior of the pericarp is colored closest to 155B.

The fruit pedicel at green maturity curves gradually downward. At this age the pedicel measured was 14 mm long×2 mm in diameter. The pedicel is covered with appressed, predominantly straight, ascending hairs. The pedicel widens near the receptacle to 3.5 mm in diameter. The receptacle is discoid, loosely covered in ascending, appressed and slightly erratic hairs. Receptacle is colored 199C.

Fruits contain numerous comose seeds (98 in the fruit examined). The seeds look like the scales of a fish when the fruit first opens, the seeds overlap toward the base of the fruit, while the hairs face the fruit apex attached to the seed base. Seeds are more or less lance obovate in shape, measuring 6 mm long×3-3.5 mm wide×1 mm thick. The seeds are variously cupped or slightly twisted adaxially. The adaxial surface of the seed has an obscure hilum toward the pointed end of the seed measuring about 3 mm long×0.3 mm wide running along the long axis of the seed. Hilum color is 165A. The seeds have a finely wrinkled surface and are colored 165A except for the rim. The pattern of wrinkling is somewhat radiant. Each seed has an upturned rim on the abaxial side, the rim about 0.3 mm wide and colored 165B. The 50+ soft hairs in the coma are parallel in the fruit, spreading as the fruit opens and dries. The hairs measure 22-25 mm long and less than 0.1 mm in diameter, color whiter than NN155D.

Seeds are attached to a hyaline, strongly ribbed placenta, these ribs soft and flexible. The specimen examined had 16 ribs. The ribs have a dentate margin, the teeth offset toward the fruit base. Maximum rib height is 3 mm. The placenta is lanceoloid in shape, measuring 80 mm long×6 mm wide and thick. Placenta is relatively uniformly colored 157D.

*Asclepias subulata* 'Butterfly Magic' has no known disease problems. Plants are parasitized by both the milkweed bug, *Onopeltus fasciatus* and yellow aphids, *Aphis nerii* as are all milkweeds. No plant resistance to these insects is known. Generally, both are well tolerated by the plants unless the insect numbers become overwhelming. Biological and chemical control methods are available for these insect pests.

COMPARISONS TO RELATED *ASCLEPIAS SUBULATA*

The vast majority of *Asclepias subulata* plants in the nursery trade are grown from seed and as a result are highly variable in growth habit, adaptability to cultivation, growth rates and frost/freeze hardiness. In comparison, *Asclepias subulata* 'Butterfly Magic' is uniform in growth habit, is well adapted to cultivation, has improved plant density, with an improved growth rate and excellent frost/freeze survivability (high teens/10° F.).

I claim:

1. A new and distinct *Asclepias subulata* plant substantially as described and illustrated herein.

* * * * *